United States Patent [19]

Seki et al.

[11] Patent Number: 5,698,629

[45] Date of Patent: Dec. 16, 1997

[54] PROCESS FOR THE PREPARATION OF A WATER-IN-OIL TYPE HIGH-MOLECULAR-WEIGHT POLYMER EMULSION

[75] Inventors: Susumu Seki; Wataru Fujii, both of Kanagawa, Japan

[73] Assignee: Nitto Chemical Industry Co., Ltd., Tokyo, Japan

[21] Appl. No.: 698,952

[22] Filed: Aug. 16, 1996

[30] Foreign Application Priority Data

Aug. 21, 1995 [JP] Japan .................. HEI 7-233184

[51] Int. Cl.⁶ ............................................ C08L 33/26
[52] U.S. Cl. .................. 524/827; 524/457; 524/555; 524/565; 524/759; 524/760; 524/761; 524/773; 524/801; 524/808; 524/812; 524/814; 524/828; 524/829; 524/831
[58] Field of Search ..................... 524/827, 828, 524/829, 831, 801, 808, 812, 814, 457, 759, 760, 761, 773, 555, 565

[56] References Cited

U.S. PATENT DOCUMENTS

| 4,399,253 | 8/1983 | Lattime ........................ 524/565 |
| 5,179,014 | 1/1993 | Watanabe et al. .............. 435/129 |
| 5,218,039 | 6/1993 | Stoy et al. .................... 524/827 X |
| 5,272,202 | 12/1993 | Kubo et al. .................. 524/565 |

*Primary Examiner*—Judy M. Reddick
*Attorney, Agent, or Firm*—Sughrue, Mion, Zinn, Macpeak & Seas, PLLC

[57] ABSTRACT

A process for the preparation of a water-in-oil type polymer emulsion which comprises polymerizing an acrylamide-containing monomer in a water-in-oil type emulsion. The acrylamide is prepared by hydrating acrylonitrile in the presence of a catalytic amount of nitrilehydratase.

8 Claims, 1 Drawing Sheet

PROCESS FOR THE PREPARATION OF A WATER-IN-OIL TYPE HIGH-MOLECULAR-WEIGHT POLYMER EMULSION

FIELD OF THE INVENTION

This invention relates to a process for the preparation of a water-in-oil type high-molecular-weight acrylamide polymer emulsion.

BACKGROUND OF THE INVENTION

A water-in-oil type emulsion of an acrylamide polymer is easy to handle because of a good dissolving power as compared with that of a powdered polymer. Thus, it is increasingly used as a coagulant or thickener in various fields, for example, in waste water disposal, sludge treatment, paper manufacturing or engineering works. In particular, there is a need in the art for an emulsion of a high-molecular weight polymer for use as a coagulant and in the field of paper manufacturing.

An emulsion polymer contains an oil phase. Thus, the polymer concentration in the whole emulsion is relatively low, and this is a fundamental defect of the emulsion polymer. Namely, if the monomer concentration in the water phase at the time of polymerization is increased to heighten the polymer concentration and concurrently raise the molecular weight of the polymer, the molecular weight of the polymer, on the contrary, is lowered when the concentration exceeds a certain value.

In other words, the polymer concentration in the product is inevitably reduced in order to increase the molecular weight, while the molecular weight is inevitably sacrificed in order to increase the polymer concentration.

Hitherto, this phenomenon has been considered to occur specifically in the preparation of a water-in-oil type emulsion.

SUMMARY OF THE INVENTION

It is therefore an object of the present invention to provide a water-in-oil type emulsion of a high-concentration and high-molecular weight acrylamide polymer.

As a result of an extensive investigation to overcome the above problems of the prior art, the present inventors have surprisingly discovered that a water-in-oil type emulsion of a high concentration and high molecular weight acrylamide polymer can be obtained by using an aqueous acrylamide solution prepared by an enzymatic method, to thereby achieve the present invention.

The present invention provides a process for the preparation of a water-in-oil type polymer emulsion which comprises polymerizing an acrylamide-containing monomer in an water-in-oil type emulsion. In this process, the acrylamide is prepared by hydrating acrylonitrile in the presence of a catalytic amount of nitrilehydratase.

The above-described advantages of the present invention have been achieved for the first time using acrylamide prepared by an enzymatic method. The effects of the invention cannot be obtained using the product of an aqueous acrylamide solution prepared by a conventional catalytic hydration method which employs copper or a copper compound as a catalyst. This conventional catalytic hydration method is hereinafter called a "copper catalytic method".

The difference between these two methods is considered to result from the presence or absence of impurities formed in accordance with the respective acrylamide preparation processes.

According to the present invention, a water-in-oil type emulsion of a high-concentration and high-molecular-weight acrylamide polymer can be obtained. Because the monomer concentration in the water phase is 30 wt. % or more upon preparation, the advantages of the present invention are apparent. Due to its ease of handling, the water-in-oil type emulsion polymer of the present invention is therefore suitable as a coagulant for industrial waste water or sewage disposal, as a retention aid in paper manufacturing or as a filtering aid, which applications require a polymer having a high molecular weight.

DETAILED DESCRIPTION OF THE INVENTION

Figure 1:
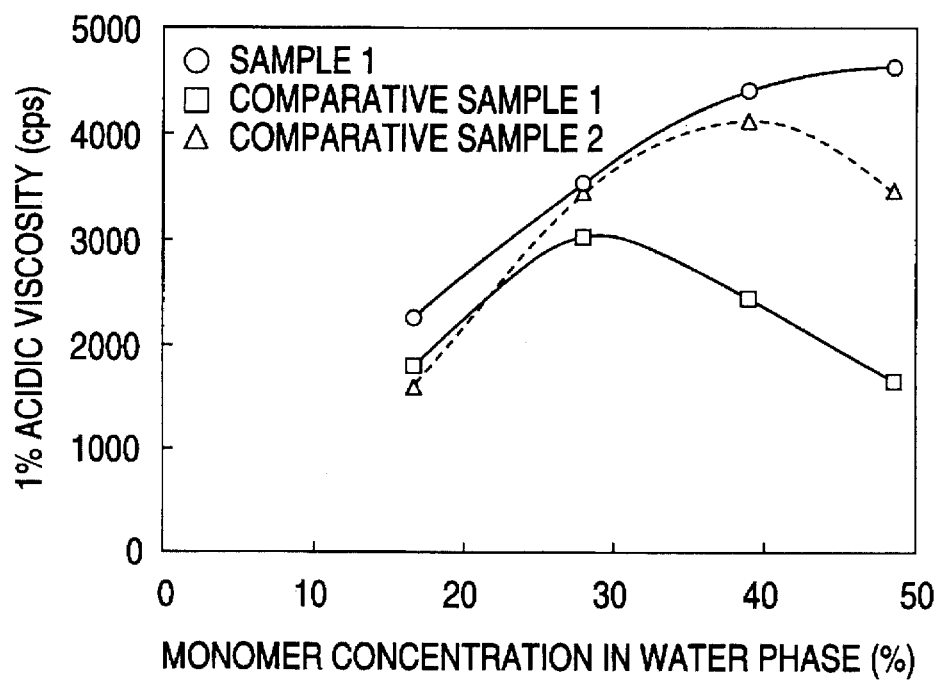
FIG. 1 illustrates the relationship between monomer concentration (%) in the water phase and 1% acidic viscosity (cps).

Acrylamide for use in the present invention is prepared by hydrating acrylonitrile via the catalytic action of nitrilehydratase.

Nitrilehydratase is an enzyme which converts a nitrile compound into its corresponding amide. Examples of the nitrilehydratase include those derived from microorganisms belonging to the genus Bacillus, genus Bacteridium, genus Micrococcus, genus Brevibacterium (JP-B-62-21519) (the term "JP-B" as used herein means an "examined Japanese patent publication"), genus Corynebacterium, genus Nocardia (JP-B-56-17918), genus Pseudomonas (JP-B-59-37951), genus Rhodococcus, genus Microbacterium (JP-B-4-4873), genus Rhodococcus (JP-B-4-40948), *Rhodococcus rhodochrous* sp. (JP-B-6-55148, SU 173184), genus Fusarium (JP-A-64-86889) (the term "JP-A" as used herein means an "unexamined published Japanese patent application") and genus Agrobacterium (JP-A-5-103681, and JP-A-6-14786).

Nitrilehydratase can be used in various forms including, for example, a culture solution of the above microorganism, a resting cell or immobilized cell separated from a culture solution, or nitrilehydratase active enzyme which is extracted from a resting cell, or which is extracted from a resting cell and then immobilized on a carrier.

No particular limitations are imposed on the reaction conditions for hydrating acrylonitrile into acrylamide so long as they allow the enzymatic reaction to proceed at normal temperature and normal pressure. An aqueous acrylamide solution after the hydrating reaction can be polymerized as is or after increasing the acrylamide concentration by a condensation operation.

The water-in-oil type emulsion polymerization according to the present invention is conducted with a water phase composed of an aqueous solution of an acrylamide-containing monomer that is dispersed in an oil phase composed of a hydrophobic liquid and a water-in-oil type emulsifier. The water-in-oil type polymer emulsion can be obtained in a form wherein the polymer-containing water phase is dispersed as fine particles having a particle size of 100 μm or smaller.

The monomer in the water phase can be composed of acrylamide along or in combination with a vinyl monomer that is copolymerizable with acrylamide. The higher the proportion of acrylamide or the higher the monomer concentration in the water phase, the more prominent the effects of the present invention and the higher the molecular weight of the resultant water-in-oil type polymer emulsion. Specifically, the proportion of acrylamide is 50 mol % or more, and the monomer concentration in the water phase is generally 30 wt. % or more, preferably 40 wt. % or more.

Examples of the vinyl monomer copolymerizable with acrylamide include water soluble monomers, for example, quaternary ammonium salts of a cationic monomer, e.g., methacrylamide, 2-acrylamide-2-methylpropane sulfonic acid (sulfonate), acrylic acid (acrylate), dimethylaminoethyl (meth)acrylate, diethylaminoethyl (meth)acrylate, dimethylaminopropyl (meth)acrylate, dimethylaminohydroxypropyl (meth)acrylate, dimethylaminoethyl acrylamide or methacryloyloxyethyl trimethylammonium chloride, and vinylpyrolidone. In addition, sparingly-soluble or hydrophobic monomers, for example, acrylonitrile, methyl methacrylate or styrene can also be added to the extent that the water solubility of the target polymer is not deteriorated.

Examples of the hydrophobic liquid of the oil phase include liquid hydrocarbons and substituted liquid hydrocarbons. Preferred are halogenated hydrocarbons, for example, perchloroethylene, and aromatic and aliphatic hydrocarbons, for example, benzene, xylene, kerosine and liquid paraffin. Aliphatic hydrocarbons are particularly preferred.

Preferred examples of the emulsifiable surfactant that is used as an emulsion formation agent include those having a hydrophile-lyophile balance (HLB) of from 1 to 10, preferably from 2 to 6. Specific examples thereof include sorbitan monooleate, sorbitan monostearate, polyoxyethyelene sorbitan monooleate, polyoxyethylene oleyl ether and polyoxyethylene nonyl phenyl ether and mixtures thereof.

To obtain a stable emulsion, the emulsifying surfactant is generally added in an amount of 1.0 wt. % to 20.0 wt. %, preferably 2.0 wt. % to 15.0 wt. %, based on the total weight of the hydrophobic liquid.

The proportion of the water phase in the emulsion according to the present invention is generally within a range of from 50 wt. % to 90 wt. %, preferably from 55 wt. % to 80 wt. % based on the emulsion. The monomer concentration of the emulsion is generally within a range of from 30 wt. % to 80 wt. %, preferably from 30 wt. % to 70 wt. %.

The emulsion can be formed by mechanically stirring the above mixture system in a WARING blender or the like.

There is no particular limitation imposed on the preparation process of the water-in-oil type polymer emulsion. Known techniques can be used, for example, such as the process disclosed by Banderhof in JP-B-34-10644 (the term "JP-B" as used herein means an "examined Japanese patent publication"). Specifically, a monomer-containing water phase and a hydrophobic liquid are mixed, emulsified and dispersed using an emulsifiable surfactant. Then, the resultant water-in-oil type emulsion is polymerized in the presence of a polymerization initiator which forms a free radical, to thereby obtain a water-in-oil type polymer emulsion of the present invention.

Exemplary polymerization initiators include redox initiators each of which contains both a peroxidation agent, for example, persulfate or alkyl peroxide, and a reducing agent, for example, sulfite, ferrous salt or an amine compound; azo-type thermal decomposition initiators, for example, azobisisobutylonitrile, 2,2'-azobis-(2-amidinopropane) hydrochloride or 4,4'-azobis-(4-cyanovaleric acid); and photosensitizers, for example, benzophenone or benzoin methyl ether. Concerning the photosensitizer, the emulsion is exposed to light in the presence of the photosensitizer to thereby effect polymerization. The polymerization initiator may be added in an amount of from 10 ppm to 5000 ppm, preferably from 30 ppm to 3000 ppm, based on the amount of the monomer. Upon polymerization, it is possible to add, in addition to the above-described components, a chain transfer agent, a surfactant for inversion, a chelating agent, a buffer and/or a salt as needed.

The water-in-oil type polymer emulsion thus obtained can be converted into its corresponding aqueous polymer solution by adding the emulsion to a water medium containing a surfactant for inversion; or by adding the surfactant for inversion to the emulsion, followed by addition of the resultant emulsion to a water medium.

The present invention is now illustrated in greater detail with reference to the following Examples. However, it is not intended that the present invention be limited to the these Examples. All the percents are by weight unless otherwise indicated.

(Preparation of acrylamide by enzymatic method)

PREPARATION EXAMPLE 1

(1) Preparation of a J-1 strain biocatalyst:

The *Rhodococcus rhodochrous* J-1 strain (FERM-BP 1478) described in JP-B-6-55148 was inoculated on a medium described below, followed by culturing at 30° C. for 72 hours. The cells thus obtained were separated and washed, and then immobilized with a polyacrylamide gel in a manner well known in the art, to thereby obtain a biocatalyst.

| Glucose | 10 g/l |
|---|---|
| $K_2HPO_4$ | 0.5 g/l |
| $KH_2PO_4$ | 0.5 g/l |
| $MgSO_4.7H_2O$ | 0.5 g/l |
| Yeast extract | 1.0 g/l |
| Peptone | 7.5 g/l |
| Urea | 7.5 g/l |
| $CoCl_2$ | 10 mg/l |

(2) Preparation of an aqueous acrylamide solution:

The J-1 strain biocatalyst thus obtained was suspended in ion exchange water. Then, acrylonitrile was successively added under stirring at pH 7 and 5° C., to thereby obtain an aqueous solution having an acrylamide concentration of about 30%. After the reaction was completed, the biocatalyst was removed and the mixture was then filtered through a 0.45 μm filter. The filtrate was concentrated under reduced pressure, to thereby obtain a 50% aqueous solution of acrylamide (sample 1).

PREPARATION EXAMPLE 2

(1) Preparation of a B-23 strain biocatalyst:

The *Pseudomonas chlororaphis* B-23 strain (FERM-BP 187) described in JP-B-59-37951 was inoculated on the medium described below, followed by culturing at 25° C. for 48 hours. The cells thus obtained were separated and washed, and then immobilized with a polyacrylamide gel in a manner well known in the art, to thereby obtain a biocatalyst.

| Sucrose | 30 g/l |
|---|---|
| $K_2HPO_4$ | 1.0 g/l |
| $KH_2PO_4$ | 1.0 g/l |
| $MgSO_4.7H_2O$ | 1.0 g/l |
| $FeSO_4.7H_2O$ | 0.05 g/l |
| Yeast extract | 1.0 g/l |
| Mieki (flavor liquid) | 20 g/l |

(2) Preparation of an aqueous acrylamide solution:

A 50% aqueous solution of acrylamide (Sample 2) was obtained in a manner similar to Preparation Example 1, except for use of the B-23 strain as a biocatalyst instead of the J-1 strain.

(Preparation of a water-in-oil type polymer emulsion)

EXAMPLES 1–8 AND COMPARATIVE EXAMPLES 1–8

(1) Monomers used:

Sample 1 (a 50% aqueous acrylamide solution prepared according to the enzymatic method)

Sample 2 (a 50% aqueous acrylamide solution prepared according to the enzymatic method)

Comparative Sample 1 (a 50% aqueous acrylamide solution prepared according to the copper catalytic method (product of Mitsubishi Chemical Co., Ltd.))

Comparative Sample 2 (a 50% aqueous acrylamide solution prepared according to the copper catalytic method (product of Mitsui Toatsu Chemicals Inc.)

(2) Preparation of an emulsion:

In each example, a predetermined amount of the aqueous acrylamide solution (for example, 307.9 g of the 50% aqueous acrylamide solution when the monomer concentration in the water phase is 48.6%) was weighed to provide a monomer concentration in the water phase as shown in Table 1. After pH adjustment to pH 7, water was added to a total amount of 316.8 g. To the resultant water phase, 114.6 g of liquid hydrocarbon ("Isozole 400", trade name; product of Nippon Petrochemicals Co., Ltd.) and 8.8 g of an emulsifier ("Span 80", trade name) were added, followed by preliminarily emulsifying for about three minutes using a magnetic stirrer. Emulsification was conducted for 30 minutes in a WARING blender at a stirring rate of 14,700 rpm to prepare an emulsion.

(3) Polymerization:

An emulsion in an amount of 400 g prepared as described above was charged to a 500-ml separable flask equipped with a stirrer, a nitrogen gas blowing inlet, a thermocouple and a gas outlet. After a water bath was heated to the polymerization initiation temperature, nitrogen purging was started while stirring at a rate of 240 rpm. An initiator (100 ppm/emulsion of a solution of 1% benzoinethyl ether (BBE) in methanol) was added and nitrogen purging was conducted for 30 minutes. The resultant mixture was then exposed to a UV (ultraviolet) lamp to thereby start polymerization. The polymerization temperature was regulated to not exceed 40° C. by turning the UV lamp on or off by means of a temperature controller. Polymerization was continued until the amount of the remaining monomer became 1% or lower.

(4) Addition of an inversion reagent after polymerization and measurement of the viscosity of the polymer:

After polymerization, the polymer emulsion was weighed in a 500-ml beaker to provide a polymer concentration of 1% at the time of viscosity measurement, followed by addition of water to a total amount of 500 g. To the resulting solution, a 12% aqueous solution of an inversion reagent ("Emulgen 810": "Emulgen 913"=2:1) was added in a concentration of 21% based on the amount of the emulsion while stirring at 240 rpm. The stirring was conducted for 8 hours to thereby complete the inversion. To the inverted reaction mixture, 10 ml of 2N sulfuric acid were added and the viscosity (1% acidic viscosity) under acidic conditions was measured using a B-type viscometer (product of Tokyo Keiki Co., Ltd.).

(5) Measurement of coagulation performance (sedimentation half-value period):

In a 100-ml beaker, 3 g of kaolin and 80 g of ion exchange water were weighed, followed by stirring with a magnetic stirrer. The reaction mixture was adjusted to pH 6.2 to 6.5 with 0.1N NaOH, followed by stirring for about one minute. The reaction mixture was then poured into a settling tube, and ion exchange water was added thereto to a total amount of 100 ml. An aqueous polymer solution which had been diluted to a polymer concentration of 0.1% was added to the settling tank so that the amount of the polymer became 1.5 ppm based on the total amount of the liquid. The settling tube was turned upside down twenty times by an end-over-end mixer, and then was allowed to stand. The time (seconds) required to settle the flock thus formed until the upper end thereof reached a scale of 50 ml was measured.

The results are shown in Table 1 below and in FIGS. 1 and 2.

TABLE 1

| Experiment No. | Monomer | Monomer Concentration (water phase) (%) | 1% Acidic Viscosity (cps) | Sedimentation half-value period (sec) |
| --- | --- | --- | --- | --- |
| Example 1 | Sample 1 | 48.6 | 4600 | 30 |
| Example 2 | Sample 1 | 38.9 | 4400 | — |
| Example 3 | Sample 1 | 27.8 | 3300 | — |
| Example 4 | Sample 1 | 16.7 | 2250 | — |
| Example 5 | Sample 2 | 48.6 | 4600 | 30 |
| Example 6 | Sample 2 | 38.9 | 4500 | — |
| Example 7 | Sample 2 | 27.8 | 3100 | — |
| Example 8 | Sample 2 | 16.7 | 2100 | — |
| Comp. Ex. 1 | Comp. Sample 1 | 48.6 | 1600 | 53 |
| Comp. Ex. 2 | Comp. Sample 1 | 38.9 | 2400 | — |
| Comp. Ex. 3 | Comp. Sample 1 | 27.8 | 3000 | — |
| Comp. Ex. 4 | Comp. Sample 1 | 16.7 | 1800 | — |
| Comp. Ex. 5 | Comp. Sample 2 | 48.6 | 3400 | 40 |
| Comp. Ex. 6 | Comp. Sample 2 | 38.9 | 4100 | — |
| Comp. Ex. 7 | Comp. Sample 2 | 27.8 | 3400 | — |
| Comp. Ex. 8 | Comp. Sample 2 | 16.7 | 1600 | — |

As apparent from Table 1 and FIG. 1, in each case where the raw material of comparative samples 1 and 2 was used as the acrylamide, the 1% viscosity of the resultant polymer showed a decrease as the monomer concentration in the water phase exceeded about 30 wt. % or 40 wt. %. On the other hand, in each case where samples 1 and 2 of the invention were used, even when the monomer concentration in the water phase exceeded 40 wt. %, the 1% acid viscosity of the polymer did not show a decrease. In those cases, the viscosity was maintained at a high level, which is entirely different from the results of comparative samples 1 or 2.

Figure 2:
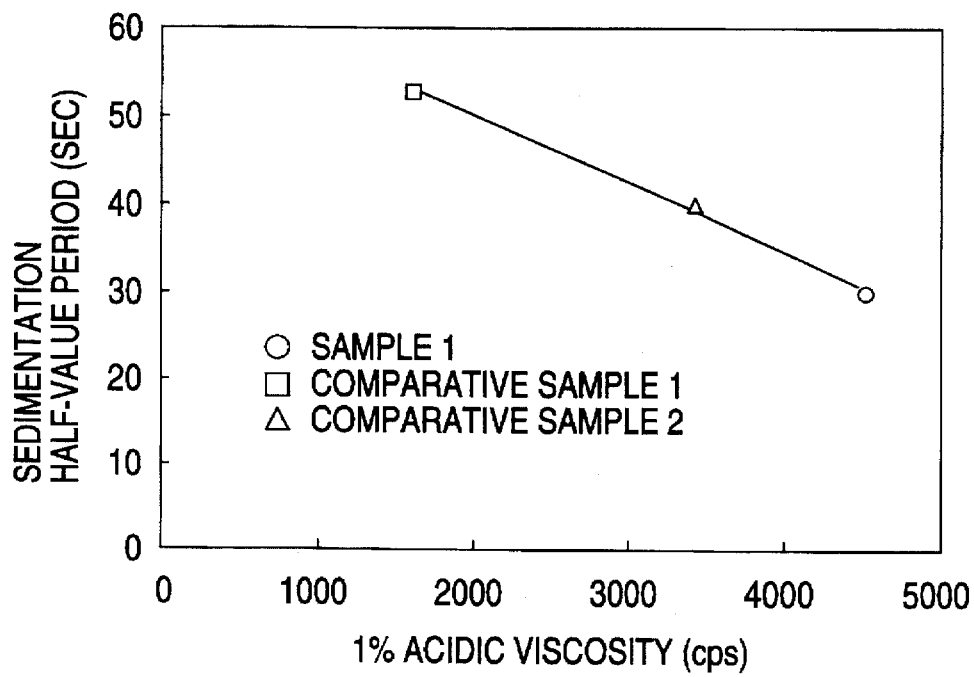
FIG. 2 illustrates the relationship between the 1% acidic viscosity (cps) and sedimentation half-value period (sec).

There is a close mutual relationship between the sedimentation half-value period of kaolin and 1% acidic viscosity of each of the polymers obtained by polymerizing at a monomer concentration of 48.6 wt. % in the water phase (FIG. 2). The above results demonstrate that a higher molecular weight was attained when samples 1 and 2 of the invention prepared by an enzymatic method were used, as compared with comparative samples 1 and 2 prepared by the copper catalytic method.

EXAMPLES 9 AND COMPARATIVE EXAMPLES 9–10

(1) Monomers used:

Sample 1 (the same as above)

Comparative Sample 1 (the same as above)

Comparative Sample 2 (the same as above)

Acrylic acid (product of Mitsubishi Petrochemical Company Limited)

(2) Preparation of an emulsion:

In 261.8 g of each of sample 1, comparative sample 1 or comparative sample 2 were incorporated 23.1 g of acrylic acid. The resulting mixture was adjusted to pH 6.3 with a 40% aqueous NaOH solution, followed by addition of water to a total amount of 316.8 g to prepare the water phase. To the water phase, 114.6 g of liquid hydrocarbon ("Isozole 400", trade name; product of Nippon Petrochemicals Co., Ltd.) and 8.8 g of an emulsifier ("Span 80:) were added, followed by preliminarily emulsifying for about three minutes using a magnetic stirrer. Emulsification was conducted for 30 seconds in a WARING blender at a stirring rate of 14,700 rpm to prepare an emulsion.

The emulsions thus obtained were subjected to step (3) to (5) of Example 1 above in accordance with the procedures of Example 1.

The results are shown in Table 2 below.

TABLE 2

| Experiment No. | Monomer | Monomer Concentration (water phase) (%) | 1% Acidic Viscosity (cps) |
| --- | --- | --- | --- |
| Example 9 | Sample 1 | 48.6 | 4000 |
| Comp. Ex. 9 | Comp. Sample 1 | 48.6 | 2500 |
| Comp. Ex. 10 | Comp. Sample 2 | 48.6 | 3100 |

EXAMPLE 10 AND COMPARATIVE EXAMPLES 11 AND 12

(1) Monomers used:

Sample 1 (the same as above)

Comparative Sample 1 (the same as above)

Comparative Sample 2 (the same as above)

Trimethylaminoethyl methacrylate hydrochloride (product of Kohjin Co., Ltd.)

(2) Preparation of emulsion:

In 246.3 g of each of sample 1, comparative sample 1 and comparative sample 2 were incorporated 30.8 g of trimethylaminoethyl methacrylate hydrochloride. Water was added to the resulting mixture to a total amount of 316.8 g to prepare a water phase. To the water phase, 114.6 g of liquid hydrocarbon ("Isozole 400", trade name; product of Nippon Petrochemicals Co., Ltd.) and 8.8 g of an emulsifier ("Span 80") were added, followed by preliminarily emulsifying for about three minutes using a magnetic stirrer. Emulsification was conducted for 30 seconds in a WARING blender at a stirring rate of 14,700 rpm to prepare an emulsion.

The emulsions thus obtained were subjected to steps (3) to (5) of Example 1 above in accordance with the procedures of Example 1.

Incidentally, the viscosity of the 1% aqueous polymer solution was measured in a manner similar to Example 1 except for using 20 g of NaCl instead of 10 ml of 2N sulfuric acid.

The results are shown in Table 3.

TABLE 3

| Experiment No. | Monomer | Monomer Concentration (water phase) (%) | 1% Salt Viscosity (cps) |
| --- | --- | --- | --- |
| Example 10 | Sample 1 | 48.6 | 3200 |
| Comp. Ex. 11 | Comp. Sample 1 | 48.6 | 2200 |
| Comp. Ex. 12 | Comp. Sample 2 | 48.6 | 3000 |

While the invention has been described in detail and with reference to specific embodiments thereof, it will be apparent to one skilled in the art that various changes and modifications can be made therein without departing from the spirit and scope thereof.

What is claimed is:

1. A process for the preparation of a water-in-oil polymer emulsion, comprising the steps of:
    (a) hydrating acrylonitrile in the presence of a catalytic amount of nitrilehydratase to obtain an acrylamide; and
    (b) polymerizing the acrylamide produced in step (a) or copolymerizing the acrylamide produced in step (a) and a monomer copolymerizable with acrylamide in a water-in-oil emulsion.

2. The process according to claim 1, wherein said water-in oil emulsion comprises a water phase having an acrylamide-containing monomer concentration of 30 wt. % or more in the water phase.

3. The process according to claim 1, wherein said water-in-oil emulsion comprises a water phase having an acrylamide-containing monomer concentration of 40 wt. % or more in the water phase.

4. The process according to claim 1, wherein said polymerizing step comprises dispersing a water phase containing said acrylamide-containing monomer into an oil phase comprising a hydrophobic liquid and an emulsifier to prepare a water-in-oil polymer emulsion.

5. The process according to claim 4, wherein the hydrophobic liquid is selected from the group consisting of halogenated hydrocarbons, aromatic hydrocarbons and aliphatic hydrocarbons, and the emulsifier is selected for the group consisting of sorbitan monooleate, sorbitan monostearate, polyethylene sorbitan monooleate, polyoxyethylene oleyl ether and polyoxyethylene nonyl phenyl ether and mixtures thereof.

6. The process according to claim 1, wherein said water-in-oil polymer emulsion comprises a polymer-containing water phase dispersed as fine particles having a particle diameter of 100 μm or smaller.

7. The process according to claim 1, wherein said hydrating step comprises adding acrylonitrile to a suspension of nitrilehydratase in water and then removing the nitrilehydratase after the hydrating reaction is complete.

8. A process for the preparation of an aqueous acrylamide polymer solution, comprising the steps of:
    (a) hydrating acrylonitrile in the presence of a catalytic amount of nitrilehydratase to obtain an acrylamide;
    (b) polymerizing the acrylamide produced in step (a) or copolymerizing the acrylamide produced in step (a) and a monomer copolymerizable with acrylamide in a water-in-oil emulsion to obtain a water-in-oil polymer emulsion; and
    (c) adding the water-in-oil polymer emulsion to a water medium containing an inversion reagent or adding an inversion reagent to the emulsion and then adding the resulting emulsion to a water medium, to thereby obtain an aqueous acrylamide polymer solution.

* * * * *